US005776934A

United States Patent [19]
Lesmann et al.

[11] Patent Number: 5,776,934
[45] Date of Patent: Jul. 7, 1998

[54] USE OF 1,3,5-TRIAZINE-2,4,6-TRIS-ALKYLAMINOCARBOXYLIC ACID DERIVATIVES AS BIOCIDAL AGENTS IN AQUEOUS SYSTEMS AND COOLING LUBRICANTS COMPRISING THESE

[75] Inventors: Jörg Lesmann; Hermann Georg Schäfer, both of Hamburg, Germany

[73] Assignee: CG-Chemie GmbH, Hamburg, Germany

[21] Appl. No.: 244,115

[22] PCT Filed: Sep. 29, 1992

[86] PCT No.: PCT/EP92/02248

§ 371 Date: May 19, 1994

§ 102(e) Date: May 19, 1994

[87] PCT Pub. No.: WO93/09670

PCT Pub. Date: May 27, 1993

[30] Foreign Application Priority Data

Nov. 19, 1991 [DE] Germany ............ 41 38 090.8

[51] Int. Cl.$^6$ ............... A01N 43/68
[52] U.S. Cl. ............... 514/245; 62/184
[58] Field of Search ............ 514/245; 62/184; 424/78.08

[56] References Cited

U.S. PATENT DOCUMENTS 4,824,845  4/1989  Gehret et al. ............ 514/245

FOREIGN PATENT DOCUMENTS 0046139  2/1982  European Pat. Off. .
0174574  3/1986  European Pat. Off. ............ 514/245
0262086  3/1989  European Pat. Off. .

OTHER PUBLICATIONS

Nestler, H., et al., "Preparation of N–(1,3,5–triazinyl)amino acid derivatives", *Chemical Abstracts*, vol. 60, Abstract No. 4145e, Col. 4144 (1964).

*Chemical Abstracts, Registry Handbook—Number Section*, (1986) Columbus US, pp. 2992, CAS RN 103479–85–2.

*Chemical Abstracts, Registry Handbook—Number Section*, (1982) Columbus US, p. 156, CAS RN 80584–91–4.

*Chemical Abstracts, Registry Handbook—Number Section*, (1982) Columbus US, pp. 156, CAS RN 80584–92–5.

*Chemical Abstracts, Registry Handbook—Number Section*, (1991) Columbus US, p. 3274, CAS RN 135043–68–4 & 135043–69–5.

*Primary Examiner*—Peter F. Kulkosky
*Attorney, Agent, or Firm*—Flehr Hohbach Test Albritton & Herbert LLP; Walter H. Dreger; Mark T. Kresnak

[57] ABSTRACT

1,3,5-Triazine-2,4,6-tris-alkylaminocarboxylic acid derivatives of the general formula (I): 1,3,5-triazine-2,4,6-tris [NH—(CH$_2$)$_n$—CO—O—R$^1$] are employed as biocidal or biostatic agents in aqueous systems, in particular in cooling lubricants. Fungicides, for example pyrithione or derivatives thereof and/or N-alkyl-diazenium dioxide salts, can be added to the aqueous systems. 0.05 to 0.40% by weight of the 1,3,5-triazine-2,4,6-alkylaminocarboxylic acid derivatives and 0.0001 to 0.2% by weight of fungicides are sufficient to maintain the biocidal or biostatic actions.

7 Claims, No Drawings

USE OF 1,3,5-TRIAZINE-2,4,6-TRIS-ALKYLAMINOCARBOXYLIC ACID DERIVATIVES AS BIOCIDAL AGENTS IN AQUEOUS SYSTEMS AND COOLING LUBRICANTS COMPRISING THESE

This application is a 371 of PCT/EP92/02248 filed Sep. 29, 1992.

The invention relates to 1,3,5-triazine-2,4,6-tris-alkylaminocarboxylic acid derivatives, their use as biocidal or biostatic agents in aqueous systems and cooling lubricants comprising these. The triazinetricarboxylic acids on which the derivatives are based, that is to say the 2,4,6-tris(omega'-carboxyalkylamino)-1,3,5-triazines, called 1,3,5-triazine-2,4,6-tris-alkylaminocarboxylic acids below, are described in J. Prakt. Chemie, 23 (1963), pages 173 to 185 and in EP-B 0 046 139. EP-B 0 046 139 furthermore relates to the use of the triazinetricarboxylic acids mentioned and alkali metal and mono-, di- or triethanolammonium salts thereof as corrosion inhibitors in aqueous systems.

An anticorrosion agent which comprises an imidazoline, one of the triazinetricarboxylic acids mentioned and at least one mono-, di- or trialkanolamine and water is described in EP-A 0 262 086. The corrosion inhibitors according to EP-B 0 046 139 and EP-A 0 262 086 are added to aqueous systems, for example cooling liquids, cooling lubricants, paints or cleaners, which in turn contain further additives, for example biocides. Additives which have been used to date are halogen-containing compounds and, for example, boric acid and reaction products of boric acid with alkanolamines, see Ullmanns Encyklopadie der technischen Chemie (Ullmann's Encyclopedia of Industrial Chemistry), 4th Edition, Volume 8, Verlag Chemie, Weinheim 1974, pages 653–655. In other cases, formaldehyde or formaldehyde derivatives have been added as biocide. However, halogen-containing compounds, boric acid and boric acid derivatives and also formaldehyde and derivatives thereof are undesirable for various reasons. There is therefore an increasing need for biocidal agents which can be used in aqueous systems and are free from halogen-containing compounds, formaldehyde, formaldehyde derivatives, boric acid or boric acid derivatives.

It has now been found that the 1,3,5-triazine-tris-2,4,6-alkylaminocarboxylic acid derivatives of the general formula

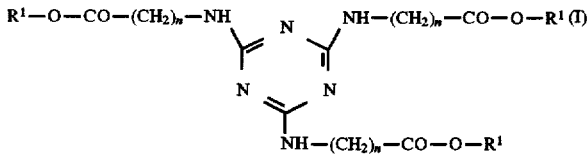

in which
n denotes a number in the range from 4 to 11 and
$R^1$ has one of the following meanings:

a) an alkali metal atom, one molar equivalent of an alkaline earth metal atom or an ammonium ion derived from an alkanolamine of the general formula $$(R^2)_3 N \quad (II)$$

in which
at least one of the groups $R^2$ denotes
aa) a hydroxyalkyl group having 2 to 4 carbon atoms,
bb) a hydroxyalkyl-oxyalkylene group having in each case 2 to 4 carbon atoms in the hydroxyalkyl and oxyalkyl radical or cc) a dihydroxyalkyl group having 3 to 6 carbon atoms and, if less than three of the groups $R^2$ have the above meaning, the other groups $R^2$ are hydrogen, or one of the groups $R^2$ has the abovementioned meanings, the second is an alkyl group having 1 to 6 carbon atoms and the third is hydrogen, b) a straight-chain or branched alkyl or alkenyl group having 1 to 23 carbon atoms, c) a cycloalkyl group having 5 to 6 carbon atoms in the cyclic radical, which is optionally substituted by an alkyl group having 1 to 4 carbon atoms or by several groups, d) a radical of a polyol having 2 to 15 carbon atoms and 2 to 6 hydroxyl groups, including addition products of ethylene oxide and/or propylene oxide onto the abovementioned polyols, e) a radical of an addition product of ethylene oxide and/or propylene oxide on straight-chain or branched alcohols having 6 to 22 carbon atoms, f) a radical of a polyethylene, polypropylene or mixed polyethylene/polypropylene glycol, the free hydroxyl group of which is optionally substituted by an alkyl group having 1 to 4 carbon atoms, g) a radical of a hydroxycarboxylic acid having 2 to 18 carbon atoms, h) a phenylalkyl group having 1 to 4 carbon atoms in the alkyl radical
or i) a radical of an alkanolamine of the general formula II can be used as biocidal or biostatic agents in aqueous systems.

According to a preferred embodiment of the invention, 1,3,5-triazine-2,4,6-tris-alkylaminocarboxylic acid derivatives of the general formula I in which n denotes a number in the range from 4 to 8, preferably the number 5, are used.

Alkali metal atoms can be lithium, sodium or potassium. Alkaline earth metal atoms can be magnesium or calcium.

The alkanolamines of the general formula II contain primary, secondary or tertiary amino and free hydroxyl groups. Both amides and esters, which are in equilibrium with one another, can be formed in the reaction of alkanolamines containing primary or secondary amino groups with carboxylic acids, see "Surfactants in Consumer Products", editor J. Falbe, Springer-Verlag, Heidelberg 1987, page 96. For clarity, the reaction products of 1,3,5-triazine-2,4,6-tris-alkylaminocarboxylic acids with alkanolamines to give compounds of the general formula I in which $R^1$ is the radical of an alkanolamine according to definition i) are represented here merely as amino esters. However, it is readily clear to the expert that the 1,3,5-triazine-2,4,6-tris-alkyl-carboxylic acid derivatives thus defined also include the corresponding alkanolamides.

Typical examples of hydroxyalkyl groups having 2 to 4 carbon atoms which can form the group $R^2$ are 2-hydroxyethyl, 1-methyl-2-hydroxyethyl, 2-hydroxypropyl, 3-hydroxypropyl, 2-hydroxybutyl, 4-hydroxybutyl and 2-methyl-2-hydroxypropyl groups; typical examples of hydroxyalkyl-oxyalkylene groups having in each case 2 to 4 carbon atoms in the hydroxyalkyl and oxyalkylene radical are hydroxyethyl-oxyethylene, hydroxypropyloxyethylene, hydroxyethyl-diethyleneoxy, hydroxyethyloxypropylene and hydroxypropyl-oxypropylene groups, and typical examples of dihydroxyalkyl groups having 3 to 6 carbon atoms are 2,3-dihydroxypropyl, 3,4-dihydroxybutyl, 1,3-dihydroxypropyl and 1,3-dihydroxy-2-methyl- or -ethyl-propyl groups; and furthermore also hydroxyethyl-, hydroxypropyl- and hydroxybutyl-oxybutylene groups.

Compounds of the general formula I in which $R^1$ denotes a radical of an alkanolamine of the general formula II or an ammonium ion derived from this alkanolamine are obtainable by reaction of 1,3,5-triazine-2,4,6-tris-alkylaminocarboxylic acids of the general formula

1,3,5-triazine-2,4,6-tris[-NH—(CH$_2$)$_n$—COOH]  (III)

in which n is as defined above,
with alkanolamines of the general formula II by processes which are known per se.

The reaction with a molar excess of the alkanolamines, based on the 1,3,5-triazine-2,4,6-tris-alkylaminocarboxylic acids, is preferred. The unreacted portion of the alkanolamines can be reacted with organic acids chosen from the group formed by straight-chain or branched, saturated or unsaturated fatty acids having 5 to 22 carbon atoms in order to establish a pH of 4.5 to 9.5. Examples of the fatty acids mentioned are pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, 10-undecenoic acid, 9c-dodecenoic acid, 9c-tetradecenoic acid, 9c-hexadecenoic acid, 6c-octadecenoic acid, 6t-octadecenoic acid, 9c-octadecenoic acid, 9t-octadecenoic acid, 9c,12c-octadecadienoic acid, 9t,12t-octadecadienoic acid, 9c,12c,15c-octadecatrienoic acid, 9c,11t,13t-octadecatrienoic acid, 9c-eicosenoic acid, 5,8,11,14-eicosatetraenoic acid, 13c-docosenoic acid, 13t-docosenoic acid, 4,8,12,15,19-docosapentaenoic acid, 12-hydroxy-octadenoic acid and 12-hydroxy-9c-octadecenoic acid, c indicating a cis double bond and t a trans double bond, as well as technical grade mixtures thereof. Fatty acids and fatty acid mixtures which are obtainable from renewable raw materials, in particular vegetable and/or animal fats and oils, for example caproic, caprylic, capric, lauric, myristic, palmitic, stearic, oleic, ricinoleic, linoleic, erucic and behenic acid, furthermore are particularly suitable.

Preferably, the unreacted portion of the alkanolamines is reacted with straight-chain or branched, saturated or unsaturated fatty acids having 5 to 11 carbon atoms. If no stable solutions or emulsions are obtained in this manner, straight-chain or branched, saturated or unsaturated fatty acids having 12 to 22 carbon atoms can additionally be used to establish the desired hydrophilic/hydrophobic balance.

Those compounds of the general formula I which contain no secondary or tertiary amino functions are preferably employed. Secondary amines and alkanolamines can form undesirable, stable nitrosamines with nitrite ions. Under certain circumstances, tertiary amines and alkanolamines can form secondary amines or alkanolamines by dealkylation. In contrast, primary amines as a rule do not form stable nitrosamines, but are used rather as trapping agents for nitrite ions because of the rapid dissociation of the nitrosamines intermediately formed. If compounds of the general formula I derived from secondary alkanolamines nevertheless are to be employed, the use of a mixture of compounds derived from primary and secondary alkanolamines is preferred, since the formation of the unstable primary nitrosamines then takes place more rapidly than that of the secondary nitrosamines.

According to another aspect, the invention thus relates to the use of compounds of the general formula I which are free from secondary or tertiary amino functions and thus cannot form stable nitroso compounds, or which, if the analogous compounds of the general formula I containing secondary or tertiary amino functions are simultaneously present, prevent the formation of stable nitroso compounds.

Biocidal and biostatic mixtures of monocarboxylic acid alkanolamides and 1,3,5-triazine-2,4,6-tris-alkyl-aminocarboxylic acid alkanolamides and if appropriate alkanolammonium salts of the monocarboxylic acids and/or of the 1,3,5-triazine-2,4,6-tris-alkylaminocarboxylic acids can also be used.

The abovementioned biocidal and biostatic mixtures can be prepared by mixing the individual components. However, they are expediently prepared by preparing the alkanolamides or alkanolammonium salts in situ from the monocarboxylic acids and the 1,3,5-triazine-tris-alkylaminocarboxylic acids of the general formula III, in which n is as defined above, with alkanolamines of the general formula II, in which R$^2$ is as defined above, preferably in an excess of the alkanolamines.

Primary alkanolamines or mixtures of primary and secondary alkanolamines are preferably used.

10 to 50 mol, in particular 10 to 30 mol, of the amines of the general formula II and 0.5 to 5 mol of the monocarboxylic acids are preferably reacted per mole of the 1,3,5-triazine-2,4,6-tris-alkylaminocarboxylic acids.

The reactions are carried out at a temperature in the range from 50° to 180° C. Alkanolammonium salts are preferably obtained at temperatures of 50° to 100° C.; alkanolamides are obtained at temperatures of >100° to 180° C., in particular 130° to 180° C.

The monocarboxylic acids used are preferably straight-chain or branched, saturated or unsaturated fatty acids having 3 to 22, in particular 12 to 22, carbon atoms, which are reacted with the alkanolamines in a first stage, followed by addition and reaction of the 1,3,5-triazine-2,4,6-tris-alkylaminocarboxylic acids in a second stage. This reaction can also be carried out in another sequence or in a single stage, although less pronounced biocidal or biostatic properties of the mixture are then obtained.

Monocarboxylic acids which are furthermore used are preferably ether-carboxylic acids of the general formula

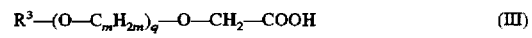
R$^3$—(O—C$_m$H$_{2m}$)$_q$—O—CH$_2$—COOH  (III)

in which
R$^3$ denotes a straight-chain or branched alkyl or alkenyl group having 9 to 18 carbon atoms, m denotes the number 2 and/or 3 and q denotes a number in the range from 0 to 100, preferably 0 to 20.

The reaction here can be carried out in any desired sequence, but also in a single stage.

Monocarboxylic acids which are likewise preferably used are arylsulphonamidocarboxylic acids of the general formula

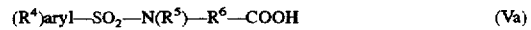
(R$^4$)aryl—SO$_2$—N(R$^5$)—R$^6$—COOH  (Va)

in which

R$^4$ denotes hydrogen or a methyl or ethyl group or several groups, R$^5$ denotes hydrogen or a methyl, ethyl, beta-cyanoethyl or hydroxymethyl group, R$^6$ denotes an alkylene group having 4 to 6 carbon atoms and aryl denotes a phenyl, naphthyl or anthracenyl radical, and/or alkylsulphonamidocarboxylic acids of the general formula

R$^7$—SO$_2$—NR$^8$—CH$_2$—COOH  (Vb)

in which R$^7$ denotes a straight-chain or branched alkyl group having 12 to 22 carbon atoms and R$^8$ denotes hydrogen or the group, —CH$_2$—COOH, and/or half-esters or half-amides of the general formula Vc

$$R^9\text{—OOC—}R^{10}\text{—COOH} \qquad (Vc)$$

in which $R^9$ is the radical of an alkanolamine of the general formula II and $R^{10}$ is an o-phenylene, vinylene or 1,2-ethylene radical. Here also, the reaction can be carried out in any desired sequence, and also in a single stage. It has not yet been possible to determine whether the sulphonamidocarboxylic acids of the general formula Va or Vb are reacted with the alkanolamines of the general formula II to give sulphonamidocarboxylic acid aminoalkyl esters, to give sulphonamidocarboxylic acid alkanolamides or to give mixtures thereof. For simplicity, these reaction products are always called alkanolamides. The abovementioned sulphonamidocarboxylic acids are known, for example, from DE-C 28 40 112 and DE-A 33 04 164.

Excess alkanolamine contained in the resulting reaction mixture can then be reacted with fatty acids having 3 to 22, preferably 3 to 11, carbon atoms, ethercarboxylic acids of the general formula IV, in which $R^3$, m and q are as defined above, and/or aryl- or alkylsulphonamidocarboxylic acids of the general formula Va or Vb, in which $R^4$, $R^5$, $R^6$, $R^7$, $R^8$ and $R^9$ are as defined above, to establish a pH in the range from 4.5 to 9.5.

It is preferable to carry out all the reactions such that the reaction mixture is always kept liquid. This is achieved, for example, with the preferred large excess of alkanolamines.

Finally, the fungicides described below can also be added to the reaction mixture after the reaction, preferably in an amount of 1 part by weight of fungicides per 10 to 100 parts by weight of the 1,3,5-triazine-2,4,6-tris-alkylaminocarboxylic acid derivatives of the general formula I, in which $R^1$ and n are as defined above, contained in the biocidal or biostatic mixture.

An excess of alkanolamines present after the reaction explained above is completely or partly neutralized, as mentioned above, to establish a suitable pH range and with the formation of further contents of alkanolamides or alkanolammonium salts.

Examples of straight-chain or branched, saturated or unsaturated fatty acids having 3 to 22 carbon atoms are propanoic acid, the abovementioned fatty acids having 5 to 22 carbon atoms and technical grade mixtures thereof. The reaction products of the alkanolamines with the monocarboxylic acids furthermore can serve as anti-corrosion agents in the aqueous system.

Preferred examples of alkanolamines of the general formula II, in which $R^2$ is as defined above, which can be used according to the invention are mono-, di- and triethanolamine, mono-, di- and tripropanolamine, mono-, di- and triisopropanolamine, 2-amino-1-butanol, 2-(2'-aminoethoxy)ethanol, 2-amino-2-methyl-1-propanol and 2-amino-2-ethyl-1,3-propanediol; as already mentioned, alkanolamines having primary amino groups or mixtures thereof with alkanolamines having secondary amino groups are particularly preferred.

Secondary alkanolamines which, in addition to having a single hydroxyalkyl, hydroxyalkyl-oxyalkylene or dihydroxyalkyl group according to the definitions given above for $R^2$, are substituted by an alkyl group having 1 to 6 carbon atoms, for example methyl, ethyl, n-propyl, i-propyl, n-butyl, i-butyl, pentyl, cyclopentyl, hexyl or cyclohexyl, furthermore are preferred.

Such secondary monoalkanol-monoalkylamines are commercially available; typical representatives are methyl-hydroxyethyl-amine, n-butyl-hydroxyethylamine and cyclohexyl-hydroxyethyl-amine and the correspondingly substituted hydroxypropyl derivatives. Some of the compounds of the general formula I derived from these monoalkanolmonoalkylamines have pronounced fungicidal properties which render the addition of other fungicides to improve the biostatic properties superfluous.

Examples of alkylene groups having 4 to 6 carbon atoms which can form the radical $R^6$ are butylene, pentylene, hexylene, 2-methyl-propylene, 2-methyl-butylene, 3-methyl-butylene, 2,2-dimethyl-propylene and 2,2-dimethyl-butylene groups.

Examples of straight-chain alkyl groups having 1 to 23 carbon atoms which can form the radical $R^1$ are the methyl, ethyl, propyl, butyl, pentyl, hexyl, heptyl, octyl, nonyl, decyl, undecyl, dodecyl, tridecyl, tetrais decyl, pentadecyl, hexadecyl, heptadecyl, octadecyl, nonadecyl, eicosyl, heneicosyl, docosyl and tricosyl group. Examples of branched alkyl groups having 1 to 23 carbon atoms are the isopropyl, isobutyl, sec-butyl, tert-butyl, 1-methyl-butyl, 2-methyl-butyl, 3-methylbutyl (isoamyl), 1-ethyl-propyl, 1,1-dimethyl-propyl, 1,2-dimethyl-propyl and 2,2-dimethyl-propyl group and the 2-branched longer-chain alkyl groups, such as the 2-methyl-pentyl, 2-ethyl-hexyl, 2-propyl-heptyl, 2-butyl-octyl, 2-pentyl-nonyl, 2-hexyl-decyl, 2-heptyl-undecyl, 2-octyldodecyl and 2-nonyl-tridecyl group. Examples of straight-chain alkenyl and alkynyl groups are the vinyl, allyl, 2-buten-1-yl and 2-propyn-1-yl groups and the longer-chain alkenyl groups, such as the 10-undecen-1-yl, 9c-octadecen-1-yl, 9t-octadecen-1-yl, 9c-octadecen-12-ol-1-yl, 9c,12c-octadecadien-1-yl, 9c,12c,15c-octadecatrien-1-yl, 9c-eicosen-1-yl, 5,8,11,14-eicosatetraen-1-yl, 13c-docosen-1-yl and 13t-docosen-1-yl group, c indicating a cis double bond and t a trans double bond. Examples of branched alkenyl groups are the 3-buten-2-yl and the 9c-octadecen-1-ol-12-yl group.

According to another preferred embodiment of the invention, $R^1$ is a 2-ethyl-hexyl group.

Compounds of the general formula I in which $R^1$ is a straight-chain or branched alkyl or alkenyl group having 1 to 23 carbon atoms can be prepared by esterification of the 1,3,5-triazine-2,4,6-tris-alkylaminocarboxylic acids with the corresponding alcohols. If the esterification is carried out with a molar excess of 2-propyn-1-ol (propargyl alcohol), based on the 1,3,5-triazine-2,4,6-tris-alkylaminocarboxylic acids, the excess propargyl alcohol acts as corrosion protection. The alcohols in turn are obtainable by the most diverse processes, for example the oxo process, the Ziegler process and the Guerbet process, and by hydrogenation of naturally occurring, animal and/or vegetable fats and oils. Examples of these alcohols are hexanol, heptanol, octanol, nonanol, decanol, dodecanol, tetradecanol, hexadecanol, octadecanol, eicosanol, docosanol, 2-methylpentanol, 2-ethyl-hexanol, 2-propyl-heptanol, 2-butyl-octanol, 2-pentyl-nonanol, 2-hexyl-decanol, 2-heptyl-undecanol, 2-octyl-dodecanol, 2-nonyl-tridecanol, 1,12-octadecanediol, 10-undecen-1-ol, 9c-octadecen-1-ol, 9t-octadecen-1-ol, 9c-octadecene-1,12-diol, 9c,12c-octa-decadien-1-ol, 9c,12c,15c-octadecatrien-1-ol, 9c-eicosen-1-ol, 5,8,11,14-eicosatetraen-1-ol, 13c-docosen-1-ol and 13t-docosen-1-ol, c indicating a cis double bond and t a trans double bond, and technical grade mixtures thereof.

According to another preferred embodiment of the invention, 1,3,5-triazine-2,4,6-tris-alkylaminocarboxylic acid derivatives of the general formula I in which $R^1$ is a straight-chain or branched alkyl or alkenyl group having 12 to 18 carbon atoms are used.

Examples of cycloalkyl groups having 5 to 6 carbon atoms in the cyclic radical which are optionally substituted by an alkyl group having 1 to 4 carbon atoms or several groups are the cyclopentyl, cyclohexyl, 1-, 2-, 3- and 4-methylcyclohexyl and the 3,3,5-trimethyl-cyclohexyl group, it being possible for the substituents to be either in the cis or in the trans position. The compounds of the general formula I in which $R^1$ has the meaning given can be prepared by esterification of the 1,3,5-triazine-2,4,6-tris-alkylaminocarboxylic acids with the corresponding alcohols, for example cyclopentanol or cyclohexanol.

Examples of polyols having 2 to 15 carbon atoms and 2 to 6 hydroxyl groups are ethylene glycol, propylene glycol, glycerol, di-, tri- and tetraglycerol, di- and trimethylolpropane, pentaerythritol, di- and tripentaerythritol, arabitol, adonitol, xylitol, sorbitol, mannitol and dulcitol. Examples of addition products of ethylene oxide or propylene oxide on one of these polyols are di-, tri- and tetraethylene glycol and di-, tri- and tetrapropylene glycol. The polyols mentioned are reacted in a molar excess, based on the polyols, with the 1,3,5-triazine-2,4,6-tris-alkylaminocarboxylic acids, so that as a rule an ester group is formed with only one hydroxyl group of the polyols.

According to another preferred embodiment of the invention, 1,3,5-triazine-2,4,6-tris-alkylaminocarboxylic acid derivatives of the general formula I in which $R^1$ is a radical of a polyol chosen from the group formed by ethylene glycol, propylene glycol, glycerol, trimethylolpropane and pentaerythritol are used.

According to another preferred embodiment of the invention, 1,3,5-triazine-2,4,6-tris-alkylaminocarboxylic acid derivatives of the general formula I in which $R^1$ is a radical of a polyethylene glycol or polypropylene glycol having a molecular weight in the range from 106 to 1000 are used.

$R^1$ can also be a radical of a mixed polyethylene/polypropylene glycol having the abovementioned molecular weight. The free hydroxyl group of the radical of a polyethylene glycol, polypropylene glycol or mixed polyethylene/polypropylene glycol furthermore can be substituted by an alkyl group having 1 to 4 carbon atoms, for example the methyl, ethyl, propyl, isopropyl, butyl, isobutyl, sec-butyl or tert-butyl group.

Examples of straight-chain or branched, saturated or unsaturated fatty alcohols having 6 to 22 carbon atoms have already been given above. The addition products of ethylene oxide and/or propylene oxide on these alcohols can also be reacted with the 1,3,5-triazine-2,4,6-tris-alkylaminocarboxylic acids.

According to another preferred embodiment of the invention, 1,3,5-triazine-2,4,6-tris-alkylaminocarboxylic acid derivatives of the general formula I in which $R^1$ is a radical of an addition product of 2 to 50, in particular 2 to 20, mol of ethylene oxide and/or propylene oxide on straight-chain or branched fatty alcohols having 12 to 18 carbon atoms are used.

Phenylalkyl groups having 1 to 4 carbon atoms in the alkyl radical are, for example, the benzyl, 1-phenyl-ethyl and 2-phenyl-ethyl group. Compounds of the general formula I, in which $R^1$ has one of the meanings given, can be prepared by reaction of the 1,3,5-triazine-2,4,6-tris-alkylaminocarboxylic acids with the corresponding alcohols; the benzyl group is preferred.

Typical representatives of hydroxycarboxylic acids having 2 to 18 carbon atoms are, for example, 12-hydroxy-9-octadecenoic acid (ricinoleic acid) or 12-hydroxy-octadecanoic acid (12-hydroxystearic acid), which are likewise reacted in a molar excess with the 1,3,5-triazine-2,4,6-tris-alkylaminocarboxylic acids to give compounds of the general formula I in which $R^1$ is a radical of a hydroxycarboxylic acid having 2 to 18 carbon atoms.

The biocidal and biostatic action of the 1,3,5-triazine-2,4,6-tris-alkylaminocarboxylic acid-derivatives used according to the invention extends to bacteria, yeasts and fungi. The limits between a biocidal and a biostatic action merge here. Either the biocidal (germ-destroying) or the biostatic (growth-inhibiting) action predominates, depending on the amounts used and the duration of action. If a fungicide is also used in addition to the 1,3,5-triazine-2,4,6-tris-alkylaminocarboxylic acid derivatives, synergistic effects occur, that is to say the actions are mutually intensified. Examples of fungicides are pyrithione and derivatives thereof, N-alkyl- or N-aryl-, in particular N-cyclohexyl-diazenium dioxide salts, for example with potassium, aluminium, tin or copper as the metal component (Ullmanns Encyklopädie der technischen Chemie (Ullmann's Encyclopedia of Industrial Chemistry), 4th edition, volume 17, Verlag Chemie, Weinheim 1979, page 369), phenols, cresols, 1,2-benzisothiazolin-3-one and derivatives thereof and 2-methyl- and 2-octyl-4-isothiazolin-3-one, halogen-free compounds being preferred. Fungicides which are water-soluble and stable to alkali furthermore are preferably employed.

According to another preferred embodiment of the invention, pyrithione or derivatives thereof and/or N-alkyl- or N-aryl-, in particular N-cyclohexyl-diazenium dioxide salts, for example with potassium, aluminium, tin or copper as the metal component, are used as the fungicides. Pyrithione is the abbreviated name for 2-pyridine-thiol 1-oxide, which is in tautomeric equilibrium with 1-hydroxy-2-pyridinethione. Possible derivatives of pyrithione are the ammonium, sodium, magnesium and zinc salts and 2,2'-dithiobis(pyridine 1,1'-dioxide), the disulphide of pyrithione. Under certain circumstances, the anion of pyrithione can be precipitated with heavy metals. In contrast, the abovementioned N-alkyl- and N-aryl-diazenium dioxide salts also have complexing properties, in addition to fungicidal properties. A mixture of pyrithione or derivatives thereof and the abovementioned N-alkyldiazenium dioxide salts is therefore preferably used. However, it is also possible to employ only pyrithione or derivatives thereof, the fungicidal action being retained in the absence of significant amounts of heavy metals. Since combinations of the fungicides mentioned with the 1,3,5-triazine-2,4,6-tris-alkylaminocarboxylic acid derivatives according to the invention show synergistic effects, very small amounts thereof are adequate for the use according to the invention in aqueous systems.

According to another preferred embodiment of the invention, the aqueous systems contain 0.05 to 0.40% by weight of the 1,3,5-triazine-2,4,6-tris-alkylaminocarboxylic acid derivatives and 0.0001 to 0.2% by weight, preferably 0.001 to 0.1, in particular 0.001 to 0.02% by weight, of fungicides, based on the total formulation.

Uses in virtually any desired aqueous or water-containing systems are possible, for example in metal-working liquids, coolants for cooling circulations, cleaning agents, hydraulic fluids, cosmetics and paints. For use in cosmetics, these are preferably adjusted to a pH in the range from 4.5 to 7.0 by the process described above. In contrast, cooling lubricants are preferably adjusted to a pH in the range from 7.5 to 9.5.

According to another preferred embodiment of the invention, the 1,3,5-triazine-2,4,6-tris-alkylaminocarboxylic acid derivatives are used in cooling lubricants.

Cooling lubricants are aqueous liquids which are used for cooling and lubrication, for example, during drilling, grinding, milling, turning, cutting, sawing, abrading or thread cutting or during rolling or drawing of metals. These can be classified into three groups, according to the mineral oil content:

a) synthetic cooling lubricants which are free from mineral oil,
b) semi-synthetic cooling lubricants which comprise about 10 to 60% by weight of mineral oil and
c) cooling lubricants which comprise about 60 to 80% of mineral oil.

The cooling lubricants furthermore can comprise polyglycols. Instead of mineral oils, it is also possible to use naturally occurring or synthetic fatty acid esters, for example rape oil or ester oils.

Further additives, such as corrosion inhibitors, copper passivators, antiwear agents, emulsifiers, carriers, precipitating agents, oxygen-trapping agents, complexing agents or foam prevention agents, can be added to all three types of cooling lubricants.

Examples of corrosion inhibitors are organic acids and salts and esters thereof, for example benzoic acid, p-tert-butylbenzoic acid, disodium sebacate, triethanolamine laurate, isononanoic acid, the triethanolamine salt of p-toluenesulphonamidocaproic acid, sodium N-lauroylsarcosinate or nonylphenoxyacetic acid, or polycarboxylic acids; nitrogen-containing substances, for example fatty acid alkanolamides, imidazolines, oxazolines, triazoles, triethanolamine, fatty amines and N-acylsarcosines, or inorganic nitrites or nitrates; phosphorus-containing substances, for example amine phosphates, phosphonic acids, phosphonates, phosphonocarboxylic acids and phosphinocarboxylic acids, or inorganic phosphates, such as $NaH_2PO_4$, and sulphur-containing substances, for example salts of petroleum-sulphonates or alkylbenzenesulphonates, or heterocyclic compounds which contain one sulphur atom or more in the ring.

Copper passivators which can be used are, for example, benzotriazoles, methylene-bis-benzotriazoles, such as sodium 2-mercaptobenzotriazole, thiadiazoles, for example 2,5-dimercapto-1,3,4-thiadiazole derivatives, or tolyltriazoles.

Antiwear agents can be AW (antiwear) or EP (extreme pressure) additives, for example substances containing sulphur, phosphorus or halogen, such as sulphonated fats and olefins, tritolyl phosphate, mono- and diesters of phosphoric acid, addition products of ethylene oxide and/or propylene oxide on polyhydroxy compounds, which are optionally partly esterified with fatty acids, chloroparaffins or ethoxylated phosphate esters, chlorine-free compounds being preferred.

Examples of emulsifiers are ether-carboxylic acids, fatty acid alkanolamides, sodium petroleum sulphonates, mono- or diesters or -ethers of polyethylene glycols, polypropylene glycols or mixed polyethylene/polypropylene glycols or fatty acid soaps.

Carriers which can be used are, for example, poly(meth) acrylic acid and its salts, hydrolysed polyacrylonitrile, polyacrylamide and copolymers thereof, ligninsulphonic acid and salts thereof, starch and starch derivatives, cellulose, alkylphosphonic acids, 1-amino-alkyl-1,1-diphosphonic acids and their salts, polymaleic acids and other polycarboxylic acids, ester oils, naturally occurring or synthetic fatty acid esters, for example rape oil, or alkali metal phosphates.

Examples of precipitating agents are alkali metal phosphates or alkali metal carbonates.

Examples of oxygen-trapping agents are alkali metal sulphates, morpholine and hydrazine.

The 1,3,5-triazine-2,4,6-tris-alkylaminocarboxylic acid derivatives according to the invention themselves have complexing properties. However, it is also possible to add other complexing agents, for example phosphonic acid derivatives, nitrilotriacetic acid or ethylenediaminetetraacetic acid and salts thereof. Furthermore, the N-alkyl- or N-aryldiazenium dioxide salts optionally to be employed as fungicides also have complexing properties, to which reference has already been made.

Examples of foam prevention agents are distearylsebacic acid diamide, distearyladipic acid diamide or ethylene oxide addition products and/or propylene oxide addition products of such amides, fatty alcohols and ethylene oxide addition products and/or propylene oxide addition products thereof, naturally occurring and synthetic waxes, silicone compounds, silicic acid derivatives and pyrogenic silicon dioxide.

The invention accordingly furthermore relates to cooling lubricants which comprise a) 1,3,5-triazine-2,4,6-tris-alkylaminocarboxylic acid derivatives of the above general formula I, in which $R^1$ and n are as defined above,
b) fungicides,
c) water,
d) if appropriate mineral oil,
e) if appropriate emulsifiers and/or other auxiliaries,
f) if appropriate corrosion inhibitors, the lubricants comprising the 1,3,5-triazine-2,4,6-tris-alkylaminocarboxylic acid derivatives in an amount of 0.05 to 0.40% by weight and the fungicides in an amount of 0.0001 to 0.2% by weight, preferably 0.001 to 0.1, in particular 0.001 to 0.02% by weight, based on the total amount of cooling lubricant.

Particularly preferred cooling lubricants are those which comprise, as emulsifiers and/or other auxiliaries a) ether-carboxylic acids of the general formula IV, in which $R^3$, m and q are as defined above, in the form of their alkanolamides and/or alkanolammonium salts with alkanolamines of the general formula II, in which $R^2$ is as defined above,
b) fatty acid alkanolamides based on straight-chain or branched, saturated or unsaturated fatty acids having 12 to 22 carbon atoms and amines of the general formula II,
c) aryl- and alkylsulphonamidocarboxylic acids of the general formula Va or Vb, in which $R^4$, $R^5$, $R^6$, $R^7$ and $R^8$ are as defined above, in the form of their alkanolamides and/or alkanolammonium salts with alkanolamines of the general formula II, in which $R^2$ is as defined above,
d) straight-chain or branched, unsaturated or saturated carboxylic acids having 5 to 22, preferably 5 to 11, carbon atoms to establish a pH in the range from 7.5 to 9.5, or
e) straight-chain or branched fatty alcohols having 12 to 18 carbon atoms.

Other particularly preferred cooling lubricants comprising pyrithione or derivatives thereof and/or N-alkyldiazenium dioxide salts as fungicides.

The cooling lubricants of the invention can be prepared by mixing the individual components together. If the cooling lubricants of the invention are to have a content of fatty acid alkanolamides, it is preferable for the compounds of the general formula I to be prepared in the manner described above in the form of their mixtures with the fatty acid alkanolamides. This process furthermore offers the advantage that exclusively liquid reaction mixtures are obtained, which can be further processed without extra measures, for example comminution or dissolving in suitable solvents.

The invention is described in more detail below with the aid of particularly preferred embodiment examples.

Examples 1 to 25 show the preparation of derivatives, used according to the invention, of 2,4,6-tris-(omega'-carboxypentylamino)-1,3,5-triazine, called triazinecarboxylic acid for short below, which is commercially obtainable or can be obtained by reaction of cyanuric chloride with the sodium salt of 6-aminohexanoic acid in accordance with EP-B 0 046 139.

The triazinecarboxylic acid can be used as the commercially available product or in the form of the commercially available aqueous product. A solid product containing about 50% by weight of water was employed in the following examples.

EXAMPLE 1

75 g (0.714 mol; 26.7 mol per mole of triazinecarboxylic acid) of diethanolamine were heated to 60° C. and 25 g (0.0267 mol) of triazinecarboxylic acid were added, while stirring, until a clear solution was formed.

100 g of a clear, low-viscosity liquid were obtained.

EXAMPLE 2

75 g (0.714 mol) of diethanolamine were stirred with 25 g (0.0267 mol) of triazinecarboxylic acid. After a reaction time of several hours at 150° to 160° C., 10 g of water were distilled off.

The final acid number was 10 mg of KOH/g.

90 g of a clear, medium-viscosity liquid were obtained.

EXAMPLE 3

75 g (1.230 mol; 46.1 mol per mole of triazinecarboxylic acid) of monoethanolamine were heated to 60° C. and 25 g (0.0267 mol) of triazinecarboxylic acid were added, while stirring, until a clear solution was formed.

100 g of a clear, low-viscosity liquid were obtained.

EXAMPLE 4

75 g (1.230 mol) of monoethanolamine were stirred with 25 g (0.0267 mol) of triazinecarboxylic acid at 60° C. and the mixture was heated to 140° to 143° C. After a reaction time of 10 hours, 18 g of water were distilled off.

The final acid number was 12 mg of KOH/g.

A white, solid product was obtained.

EXAMPLE 5

75 g (0.843 mol; 31.5 mol per mole of triazinecarboxylic acid) of 2-amino-1-butanol were heated to 60° C. and 25 g (0.0267 mol) of triazinecarboxylic acid were added, while stirring, until a clear solution was formed.

100 g of a clear, low-viscosity liquid were obtained.

EXAMPLE 6

863 g (9.697 mol; 31.5 mol per mole of triazinecarboxylic acid) of 2-amino-1-butanol were stirred with 287 g (0.307 mol) of triazinecarboxylic acid at 60° C. and the mixture was heated to 145° C. After a reaction time of 20 hours, 150 g of water were distilled off.

The final acid number was 10 mg of KOH/g.

1000 g of a clear, low-viscosity liquid were obtained.

EXAMPLE 7

75 g (0.714 mol; 26.7 mol per mole of triazinecarboxylic acid) of 2-(2'-aminoethoxy)ethanol were stirred with 25 g (0.0267 mol) of triazinecarboxylic acid at 60° C. until a clear solution was formed.

100 g of a clear, low-viscosity liquid were obtained.

EXAMPLE 8

375 g (3.571 mol; 26.7 mol per mole of triazinecarboxylic acid) of 2-(2'-aminoethoxy)ethanol were stirred with 125 g (0.134 mol) of triazinecarboxylic acid at 60° C. and the mixture was heated to 145° C. After a reaction time of 16 hours, 73 g of water were distilled off.

The final acid number was 7 mg of KOH/g.

427 g of a white, pasty product were obtained.

EXAMPLE 9

20 g (0.190 mol; 7.1 mol per mole of triazinecarboxylic acid) of 2-(2'-aminoethoxy)ethanol and 55 g (0.618 mol; 23.1 mol per mole of triazinecarboxylic acid) of 2-amino-1-butanol were heated to 60° C. and stirred with 25 g (0.0267 mol) of triazinecarboxylic acid until a clear solution was formed.

100 g of a clear, low-viscosity liquid were obtained.

EXAMPLE 10

228 g (2.171 mol; 7.1 mol per mole of triazinecarboxylic acid) of 2-(2'-aminoethoxy)ethanol and 627 g (7.045 mol; 23.1 mol per mole of triazinecarboxylic acid) of 2-amino-1-butanol were stirred with 285 g (0.304 mol) of triazinecarboxylic acid at 60° C. and the mixture was heated to 145° C. After a reaction time of 16 hours, 140 g of water were distilled off.

The final acid number was 13 mg of KOH/g.

1000 g of clear, medium-viscosity liquid were obtained.

EXAMPLE 11

75 g (0.758 mol; 28.4 mol per mole of triazinecarboxylic acid) of AMP 90 (2-amino-2-methyl-1-propanol with 10% of water) were heated to 60° C. and stirred with 25 g (0.0267 mol) of triazinecarboxylic acid until a clear solution was formed.

A clear, low-viscosity liquid was obtained.

EXAMPLE 12

833 g (8.424 mol; 31.5 mol per mole of triazinecarboxylic acid) of AMP 90 were heated to 60° C. and stirred with 250 g (0.267 mol) of triazinecarboxylic acid and the mixture was heated to 140° to 145° C. After a reaction time of 20 hours, 240 g of water were distilled off.

The final acid number was 15 mg of KOH/g.

843 g of an almost clear, high-viscosity product were obtained.

EXAMPLE 13

75 g (0.630 mol; 23.6 mol per mole of triazinecarboxylic acid) of AEPD (2-amino-2-ethyl-1,3-propanediol) were heated to 60° C. and stirred with 25 g (0.0267 mol) of triazinecarboxylic acid until a clear solution was formed.

100 g of a clear, medium-viscosity liquid were obtained.

EXAMPLE 14

990 g (8.319 mol; 23.6 mol per mole of triazinecarboxylic acid) of AEPD were heated to 60° C. and stirred with 330 g (0.353 mol) of triazinecarboxylic acid, and the mixture was heated to 140° to 145° C. After a reaction time of 16 hours, 320 g of water were distilled off.

The final acid number was 10 mg of KOH/g.

1000 g of a clear, high-viscosity liquid were obtained.

EXAMPLE 15

75 g (1.000 mol; 37.4 mol per mole of triazinecarboxylic acid) of monoisopropanolamine were heated to 60° C. and stirred with 25 g (0.0267 mol) of triazinecarboxylic acid until a clear solution was formed.

100 g of a low-viscosity liquid were obtained.

EXAMPLE 16

375 g (5.000 mol; 37.4 mol per mole of triazinecarboxylic acid) of monoisopropanolamine were heated to 60° C. and stirred with 125 g (0.134 mol) of triazinecarboxylic acid, and the mixture was heated to 140° C. After a reaction time of 16 hours, 74 g of water were distilled off.

The final acid number was 12 mg of KOH/g.

426 g of a clear, low-viscosity liquid were obtained.

EXAMPLE 17

75 g (0.503 mol; 18.9 mol per mole of triazinecarboxylic acid) of triethanolamine were heated to 60° C. and stirred with 25 g (0.0267 mol) of triazinecarboxylic acid until a clear solution was formed.

100 g of a clear, low-viscosity liquid were obtained.

EXAMPLE 18

750 g (5.034 mol; 18.9 mol per mole of triazinecarboxylic acid) of triethanolamine were heated to 60° C. and stirred with 250 g (0.267 mol) of triazinecarboxylic acid, and the mixture was heated to 140° to 145° C. After a reaction time of 16 hours, 130 g of water were distilled off.

The final acid number was 6 mg of KOH/g.

870 g of a clear, medium-viscosity liquid were obtained.

EXAMPLE 19

8 parts of triazinecarboxylic acid and 1 part of 2-(8-heptadecenyl)-4,5-dihydro-1-(2-hydroxyethyl)imidazole were added to 6 parts by weight of monoisopropanolamine at ambient temperature, while stirring. The mixture was stirred until a clear, amber-coloured liquid had formed.

EXAMPLE 20

1st Stage 130 g (1.238 mol; 4.8 mol per mole of triazinecarboxylic acid) of 2-(2'-aminoethoxy)ethanol and 370 g (4.157 mol; 16.2 mol per mole of triazinecarboxylic acid) of 2-amino-1-butanol were reacted with 190 g (0.674 mol; 2.6 mol per mole of triazinecarboxylic acid) of olein at 145° C. After a reaction time of 10 hours, 12 g of water were distilled off.

678 g of a liquid product having an acid number of 7 mg of KOH/g were obtained.

2nd Stage 678 g of the product of stage 1 were heated to 70° C. and stirred with 240 g (0.256 mol) of triazinecarboxylic acid.

A clear, viscous liquid was obtained.

EXAMPLE 20a

1st Stage 130 g (1.238 mol) of 2-(2'-aminoethoxy)ethanol and 370 g (4.157 mol) of 2-amino-1-butanol were reacted with 190 g (0.674 mol) of olein at 145° C. After a reaction time of 10 hours, 12 g of water were distilled off.

678 g of a liquid product having an acid number of 7 mg of KOH/g were obtained.

2nd Stage 678 g of the product of stage 1 were heated to 70° C. and stirred with 240 g (0.256 mol) of triazinecarboxylic acid and 174 g (0.497 mol; 1.9 mol per mole of triazinecarboxylic acid) of a commercially available arylsulphonamidocarboxylic acid having a molecular weight of about 350 (HostacorR H liquid), called sulphonamidocarboxylic acid for short below.

A stable, slightly cloudy liquid was obtained.

EXAMPLE 20b

1st Stage 130 g (1.238 mol) of 2-(2'-aminoethoxy)ethanol and 370 g (4.157 mol) of 2-amino-1-butanol were reacted with 190 g (0.674 mol) of olein at 145° C. After a reaction time of 10 hours, 12 g of water were distilled off.

678 g of a liquid product having an acid number of 7 mg of KOH/g were obtained.

2nd Stage 678 g of the product of stage 1 were heated to 70° C. and stirred with 240 g (0.0256 mol) of triazinecarboxylic acid and 106 g (0.148 mol; 0.6 mol per mole of triazinecarboxylic acid) of ether-carboxylic acid (commercially available reaction product of 1 mol of chloroacetic acid with a condensation product of 1 mol of a technical grade oleyl alcohol with 10 mol of ethylene oxide).

A clear, viscous liquid was obtained.

EXAMPLE 20c 130 g (1.238 mol) of 2-(2'-aminoethoxy)ethanol and 370 g (4.157 mol) of 2-amino-1-butanol were heated to 70° C. and the mixture was stirred with 174 g (0.497 mol) of sulphonamidocarboxylic acid and 240 g (0.256 mol) of triazinecarboxylic acid.

A pale, clear, medium-viscosity liquid was obtained.

EXAMPLE 20d 130 g (1.238 mol) of 2-(2'-aminoethoxy)ethanol, 370 g (4.157 mol) of 2-amino-1-butanol, 174 g (0.497 mol) of sulphonamidocarboxylic acid and 240 g (0.256 mol) of triazinecarboxylic acid are reacted at 145° C. After a reaction time of 12 hours, 143 g of water were distilled off.

771 g of a medium-viscosity, clear, liquid product having a final acid number of 25 mg of KOH/g were obtained.

EXAMPLE 20e 130 g (1.238 mol) of 2-(2'-aminoethoxy)ethanol and 370 g (4.157 mol) of 2-amino-1-butanol were heated to 70° C. and stirred with 106 g (0.148 mol) of ether-carboxylic acid and 240 g (0.256 mol) of triazinecarboxylic acid.

A pale, medium-viscosity liquid was obtained.

EXAMPLE 20f 130 g (1.238 mol) of 2-(2'-aminoethoxy)ethanol, 370 g (4.157 mol) of 2-amino-1-butanol, 106 g (0.148 mol) of ether-carboxylic acid and 240 g (0.256 mol) of triazinecarboxylic acid were reacted at 145° C. After a reaction time of 13 hours, 137 g of water were distilled off.

709 g of a clear, medium-viscosity product having a final acid number of 20 mg of KOH/g were obtained.

EXAMPLE 21

678 g of the liquid from the first stage of Example 20 were heated to 60° C. and stirred with 240 g (0.256 mol) of triazinecarboxylic acid and the mixture was heated to 140° to 150° C. After a reaction time of 10 hours, 138 g of water were distilled off.

The final acid number was 14 mg of KOH/g.

780 g of a clear, medium-viscosity product were obtained.

EXAMPLE 22

273 g (1.019 mol; 2.8 mol per mole of triazinecarboxylic acid) of a commercially available technical grade oleyl alcohol (about 90% strength, iodine number about 95) were heated to 80° to 100° C. and stirred slowly with 333 g (0.356 mol) of triazinecarboxylic acid, and the mixture was heated to a maximum of 200° C. After a reaction time of about 20 hours, 206 ml of water were distilled off.

The final acid number was 18 mg of KOH/g.

A clear, medium-viscosity liquid was obtained.

EXAMPLE 23

350 g (2.692 mol; 15 mol per mole of triazinecarboxylic acid) of 2-ethylhexanol were heated to 100° C. and stirred with 168 g (0.179 mol) of triazinecarboxylic acid and the mixture was heated slowly to a maximum of 190° C. After a reaction time of 10 hours, 358 g of water and ethylhexanol were distilled off.

The final acid number was 15 mg of KOH/g.

160 g of a clear, viscous liquid were obtained.

EXAMPLE 24

273 g (3.592 mol; 10.1 mol per mole of triazinecarboxylic acid) of 1,2-propylene glycol were heated to 100° C. and stirred with 333 g (0.356 mol) of triazinecarboxylic acid, and the mixture was heated to a maximum of 168° C. After a reaction time of 7 hours, 276 ml of water were distilled off.

The final acid number was 38 mg of KOH/g.

330 g of a viscous, pale liquid were obtained.

EXAMPLE 25

324 g (3.000 mol; 8.4 mol per mole of triazinecarboxylic acid) of benzyl alcohol were stirred with 333 mg (0.356 mol) of triazinecarboxylic acid and the mixture was heated under nitrogen to a maximum of 180° C. After a reaction time of 9 hours, 180 ml of water were distilled off.

The final acid number was 21 mg of KOH/g.

477 g of a low-viscosity liquid were obtained.

EXAMPLE 26

375 g (3.2 mol; 23.97 mol per mole of triazinecarboxylic acid) of N-butylethanolamine were reacted with 125 g (0.13 mol) of triazinecarboxylic acid at 145° C. After a reaction time of 14 hours, 85 g of water were distilled off.

415 g of a liquid product having an acid number of 13 mg of KOH/g were obtained.

EXAMPLE 27

167 g (1.43 mol; 8 mol per mole of triazinecarboxylic acid) of N-butylethanolamine were reacted with 167 g (0.18 mol) of triazinecarboxylic acid at 148° C. After a reaction time of 14 hours, 56 g of water were distilled off.

278 g of a viscous product with an acid number of 7 mg of KOH/g were obtained.

EXAMPLE 28

100 g (0.85 mol; 2 mol per mole of triazinecarboxylic acid) of N-butylethanolamine and 100 g (0.95 mol; 2.22 mol per mole of triazinecarboxylic acid) of 2-(2'-aminoethoxy) ethanol and 100 g (1.33 mol; 3.11 mol per mole of triazinecarboxylic acid) of monoisopropanolamine were reacted with 200 g (0.21 mol) of triazinecarboxylic acid at 150° C. After a reaction time of 10 hours, 65 g of water were distilled off.

435 g of a medium-viscosity product having an acid number of 14 mg of KOH/g were obtained.

EXAMPLE 29

516 g (4.9 mol; 8.75 mol per mole of triazinecarboxylic acid) of 2-(2'-aminoethoxy)ethanol and 248 g (3.3 mol; 5.89 mol per mole of triazinecarboxylic acid) of monoisopropanolamine were reacted with 526 g (0.56 mol) of triazinecarboxylic acid at 150° C. After a reaction time of 14 hours, 290 g of water were distilled off.

1000 g of a liquid product having an acid number of 11 mg of KOH/g were obtained.

EXAMPLE 30

1st Stage 117 g (1 mol) of N-butylethanolamine were heated to 110° C. and 148 g (1 mol) of phthalic anhydride were slowly added, while cooling. The reaction time lasted 4 hours at a maximum of 130° C.

265 g of a solid, vitreous product with an acid number of 211 mg of KOH/g were obtained.

2nd Stage 50 g of stage 1 were mixed with 50 g of product from Example 10 at 100° C.

A viscous product having an acid number of 115 mg of KOH/g was obtained.

EXAMPLE 31

50 g of Korantin PA (phthalic acid 2-methyl-2-ethylhexylamide) were mixed with 50 g of product from Example 10 at 50° C.

A viscous product having an acid number of 88 mg of KOH/g was obtained.

Comparison Examples 1 to 3 and Examples 32 to 54

A number of the 1,3,5-triazine-2,4,6-tris-alkyl-aminocarboxylic acid derivatives thus prepared were formulated with water, spindle oil and other additives stated in each case, and in some examples with fungicides, to give mixtures which result in cooling lubricants in a dilution with water of 1:20 to 1:80.

Furthermore, mixtures without biocides were formulated in Comparison Examples 1 and 2 and a mixture with a boric acid alkanolamine condensation product as the biocidal agent was formulated in Comparison Example 3.

Data in % below always relate to parts by weight.

The information in the "Exp." column relates to the explanations of Table 1. All the chemicals listed in Table 1 are commercially obtainable.

Table 1: EXPLANATIONS

1 Tall oil distillate with 25–30% resin (acid number 155–190)
2a) isononanoic acid
b) 2.2-dimethyl-octanoic acid
3 Spindle oil, viscosity: 22 m²/s at 40° C.
4a) reaction product of 1 mol of chloroacetic acid with a condensation product of 1 mol of a technical grade oleyl alcohol with 10 mol of ethylene oxide (ether-carboxylic acid)
b) reaction product of 1 mol of chloroacetic acid with a condensation product of 1 mol of $C_9$- to $C_{13}$-oxo-alcohols with 3 mol of ethylene oxide and 2 mol of propylene oxide (ether-carboxylic acid)
5a) technical grade oleyl alcohol (about 90% strength, iodine number about 95)
b) 2-hexyl-decanol
6a) condensation product of 1 mol of a technical grade mixture of oleyl and cetyl alcohol with 5 mol of ethylene oxide
b) fatty alcohol polyglycol ether (EmulsogenR LP)
7a) condensation product of 40 parts by weight of diethanolamine with 60 parts by weight of olein
b) as a) with addition of 20% of ethanolamine, based on the total amount of condensation product and ethanolamine
8a) diethylene glycol
b) butyldiglycol
c) butylglycol
9a) sodium petroleumsulphonate having a molecular weight of about 460
b) sodium alkylbenzenesulphonate having a molecular weight of about 350
10 50% strength potassium hydroxide solution
11 fungicidal mixture of 10% of the sodium salt of pyrithione 10% of N-(cyclohexyl-diazenium dioxide) potassium hydrate in the form of a 30% strength aqueous solution 10% of propylene glycol 70% of demineralized water
12 condensation product of 1 mol of boric acid with 3 mol of ethanolamine
13 arylsulphonamidocarboxylic acid having a molecular weight of about 350 (HostacorR H liquid; acid content about 90%, remainder solubilizing agent)

|  | Exp. |
|---|---|
| Comparison Example 1 | |
| 7% of fatty acids | 1 |
| 2% of sulphonates | 9b) |
| 5% of fatty acid alkanolamides | 7b) |
| 2% of auxiliaries | 8a) |
| 1% of auxiliaries | 10 |
| 83% of spindle oil | 3 |
| Comparison Example 2 | |
| 8% of fatty acids | 1 |
| 17% of sulphonates | 9a) |
| 4% of fatty acid alkanolamides | 7a) |
| 3% of auxiliaries | 8c) |
| 2% of auxiliaries | 10 |
| 36% of spindle oil | 3 |
| 30% of water | |
| Comparison Example 3 | |
| 20% of boric acid product | 12 |
| 10% of fatty acids | 1 |
| 10% of fatty acid alkanolamides | 7a) |
| 10% of auxiliaries | 8b) |
| 20% of spindle oil | 3 |
| 30% of water | |
| Example 32 | |
| 25% of Example 1 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |
| 5% of nonionic emulsifiers | 6a) |
| 1% of fungicides | 11 |
| 13% of water | |
| Example 33 | |
| 25% of Example 2 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |
| 14% of water | |
| 5% of nonionic emulsifiers | 6a) |
| Examples 34 | |
| 25% of Example 4 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |
| 5% of nonionic emulsifiers | 6a) |
| 14% of water | |
| Example 35 | |
| 22% of Example 6 | |
| 11% of fatty acids | 2a) |
| 17% of fatty acids | 1 |
| 6% of ether-carboxylic acids | 4a) |
| 9% of fatty acid alkanolamides | 7a) |
| 4% of fatty alcohols | 5a) |
| 22% of spindle oil | 3 |
| 8% of water | |
| 1% of fungicides | 11 |
| Example 36 | |
| 21% of Example 10 | |
| 21% of fatty acids | 1 |
| 11% of fatty acids | 2a) |
| 7% of ether-carboxylic acids | 4a) |
| 5% of fatty alcohols | 5b) |
| 20% of spindle oil | 3 |
| 13% of water | |
| 2% of fungicides | 11 |
| Example 37 | |
| 25% of Example 14 | |
| 31% of spindle oil | 3 |
| 10% of fatty acids | 1 |
| 3% of fatty acids | 2a) |
| 8% of fatty alcohols | 5a) |
| 5% of nonionic emulsifiers | 6a) |
| 4% of ether-carboxylic acids | 4b) |
| 1% of fungicides | 11 |
| 13% of water | |
| Example 38 | |
| 25% of Example 16 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |
| 5% of nonionic emulsifiers | 6a) |
| 1% of fungicides | 11 |

|  | Exp. |
|---|---|
| 13% of water | |
| Example 39 | 5 |
| 35% of Example 17 | |
| 20% of spindle oil | 3 |
| 10% of fatty acids | 1 |
| 5% of fatty acids | 2a) |
| 3% of ether-carboxylic acids | 4b) |
| 6% of fatty alcohols | 5b) |
| 5% of nonionic emulsifiers | 6a) |
| 16% of water | |
| Example 40 | |
| 19% of Example 21 | |
| 29% of fatty acids | 1 |
| 29% of spindle oil | 3 |
| 5% of auxiliaries | 8b) |
| 3% of nonionic emulsifiers | 6b) |
| 1% of fungicides | 11 |
| 14% of water | |
| Example 41 | |
| 20% of Example 3 | |
| 20% of fatty acids | 1 |
| 16% of fatty acids | 2a) |
| 7% of ether-carboxylic acids | 4a) |
| 5% of fatty alcohols | 5b) |
| 18% of spindle oil | 3 |
| 2% of fungicides | 11 |
| 12% of water | |
| Example 42 | |
| 21% of Example 9 | |
| 21% of fatty acids | 1 |
| 11% of fatty acids | 2a) |
| 7% of ether-carboxylic acids | 4a) |
| 5% of fatty alcohols | 5b) |
| 20% of spindle oil | 3 |
| 2% of fungicides | 11 |
| 13% of water | |
| Example 43 | |
| 7% of Example 25 | |
| 93% of Comparison Example 1 | |
| Example 44 | |
| 7% of Example 25 | |
| 91% of Comparison Example 1 | |
| 2% of fungicides | 11 |
| Example 45 | |
| 4% of Example 23 | |
| 96% of Comparison Example 1 | |
| Example 46 | |
| 4% of Example 23 | |
| 94% of Comparison Example 1 | |
| 2% of fungicides | 11 |
| Example 47 | |
| 4% of Example 23 | |
| 96% of Comparison Example 2 | |
| Example 48 | |
| 4% of Example 23 | |
| 94% of comparison Example 2 | |
| 2% of fungicides | 11 |
| Example 49 | |
| 24% of Example 20a | |
| 22% of fatty acids | 1 |
| 29% of spindle oil | 3 |
| 4% of auxiliaries | 8b) |
| 2% of monoethanolamine | |
| 4% of nonionic emulsifiers | 6a) |
| 1% of fungicides | 11 |
| 14% of water | |
| Example 50 | |
| 25% of Example 20b | |
| 23% of fatty acids | 1 |
| 29% of spindle oil | 3 |
| 3% of auxiliaries | 8b) |
| 4% of nonionic emulsifiers | 6a) |
| 1% of fungicides | 11 |
| 14% of water | |
| 1% of monoethanolamine | |
| Example 51 | |
| 23% of Example 20c | |
| 28% of fatty acids | 1 |
| 1% of fatty alcohols | 5a) |
| 4% of nonionic emulsifiers | 6a) |
| 4% of auxiliaries | 8b) |
| 1% of fungicides | 11 |
| 27% of spindle oil | 3 |
| 12% of water | |
| Example 52 | |
| 23% of Example 20d | |
| 28% of fatty acids | 1 |
| 25% of spindle oil | 3 |
| 5% of nonionic emulsifiers | 6b) |
| 2% of fatty alcohols | 5b) |
| 2% of auxiliaries | 8b) |
| 1% of fungicides | 11 |
| 14% of water | |
| Example 53 | |
| 23% of Example 20e | |
| 28% of fatty acids | 1 |
| 1% of fatty alcohols | 5a) |
| 4% of nonionic emulsifiers | 6a) |
| 4% of auxiliaries | 8b) |
| 1% of fungicide | 11 |
| 27% of spindle oil | 3 |
| 12% of water | |
| Example 54 | |
| 23% of Example 20f | |
| 28% of fatty acids | 1 |
| 1% of fatty alcohol | 5a) |
| 4% of nonionic emulsifiers | 6a) |
| 4% of auxiliaries | 8b) |
| 1% of fungicides | 11 |
| 27% of spindle oil | 3 |
| 12% of water | |
| Example 55 | |
| 21% of Example 32 | |
| 21% of fatty acids | 1 |
| 20% of spindle oil | 3 |
| 15.5% of water | |
| 1.5% of ether-carboxylic acids | 4b) |
| 2% of ether-carboxylic acids | 4a) |
| 2% of nonionic emulsifiers | 6b) |
| 5% of fatty alcohols | 5b) |
| 11% of fatty acids | 2a) |
| 1% of monoethanolamine | |
| Example 55a | |
| 98% of Example 55 | |
| 2% of fungicides | 11 |
| Example 56 | |
| 10% of Example 33 | |
| 30% of spindle oil | 3 |
| 22% of water | |
| 15% of fatty acids | 1 |
| 5% of fatty acids | 2a) |
| 5% of fatty alcohols | 5b) |
| 2% of ether-carboxylic acids | 4b) |
| 4% of ether-carboxylic acids | 4a) |
| 3% of monoethanolamine | |
| 4% of fatty acid alkanolamide | 7a) |
| Example 56a | |

-continued

| | Exp. |
|---|---|
| 98% of Example 56 | |
| 2% of fungicides | 11 |
| Example 57 | |
| | |
| 10% of Example 34 | |
| 23% of fatty acids | 2a) |
| 9% of monoethanolamine | |
| 2% of ether-carboxylic acids | 4b) |
| 6% of fatty alkanolamide | 7a) |
| 50% of water | |
| Example 57a | |
| | |
| 98% of Example 57 | |
| 2% of fungicides | 11 |
| Example 58 | |
| | |
| 5% of Example 33 | |
| 5% of Example 35 | |
| 23% of fatty acids | 2a) |
| 10% of monoethanolamine | |
| 2.5% of ether-carboxylic acids | 4b) |
| 6% of fatty acid alkanolamide | 7a) |
| 48.5% of water | |
| Example 58a | |
| | |
| 98% of Example 58 | |
| 2% of fungicides | 11 |
| Example 59 | |
| | |
| 20% of Example 37 | |
| 25% of spindle oil | 3 |
| 17% of fatty acids | 1 |
| 4% of fatty alcohols | 5b) |
| 4% of nonionic emulsifiers | 6b) |
| 1% of monoethanolamine | |
| 29% of water | |
| Example 59a | |
| | |
| 98% of Example 60 | |
| 2% of fungicides | 11 |
| Example 60 | |
| | |
| 20% of Example 37 | |
| 25% of spindle oil | 3 |
| 17% of fatty acids | 1 |
| 4% of fatty alcohols | 5b) |
| 4% of nonionic emulsifiers | 6b) |
| 1% of monoethanolamine | |
| 29% of water | |
| Example 60a | |
| | |
| 98% of Example 60 | |
| 2% of fungicides | 11 |

Microbiological test methods

An inoculation cycle test developed in-house was carried out. For this, the following dilutions of the formulations of Comparison Examples 1 to 3 and of Examples 26 to 42 were prepared with Hamburg town water: 1.25%, 2.5% and 5.0% (corresponds to 1:80, 1:40 and 1:20).

The samples were inoculated several times with a concentrated mixed germ flora. The germ flora contained bacteria, yeasts and fungi from running emulsion systems of varying origin. Their total germ count was about is $10^7$ germs/ml.

The amount of mixed germ flora for inoculation of the samples corresponded to six times the amount proposed according to DAB 9 (German Pharmacopoeia). 6 ml of germ flora were used per 100 ml of sample.

The samples were inoculated repeatedly (a maximum of 6 inoculations) by this method (in accordance with K. H. Wallhäußer; Praxis der Sterilisation-Desinfektion-Konservierung-Keimidentifizierung (Practice of Sterilization-Disinfection-Preservation-Germldentification), 4th Edition, Georg Thieme Verlag, Stuttgart 1988), until no further antimicrobial action was detectable. From experience, 1 inoculation corresponded to 3 inoculation cycles by the DAB 9/Wallhäußer method.

This method has the following advantages:

1. A mixed germ flora such as occurs in practice is employed.
2. The samples are exposed to a massive germ load several times.
3. The method is quick and therefore appropriate for industry. In comparison with the conventional method, which often takes several months, the results are available in a maximum of 8 weeks if they do not have to be repeated.
4. Conclusions as to the service lives of the emulsions in use in the central systems can be drawn from the results.

The action time of the microorganisms on the samples was about 1 week. After this time, the samples were spread out onto in each case two special nutrient media and incubated. The colony count was then determined under a microscope, and the germ count per ml of sample was determined therefrom. The number of inoculation cycles after which a first attack by germs is to be observed is shown in Table 2. This is a measure of the activity of the biocides in the particular samples. The formulations of Examples 27, 28, 29 and 32 based on the compounds of Examples 2, 4, 6 and 16 proved to be particularly active. Example 28 even shows a fungicidal action without addition of pyrithione or derivatives thereof. When Examples 26 and 36 were compared with Examples 27 and 30 respectively, it was furthermore found that, surprisingly, the alkanolamides have a better activity than the alkanolammonium salts derived from the same alkanolamines.

TABLE 2

Microbiological results

| | Dilution % | | | | | | | | | | | |
|---|---|---|---|---|---|---|---|---|---|---|---|---|
| | 1.25 | | | | 2.5 | | | | 5 | | | |
| Example | B | Y | F | IC | B | Y | F | IC | B | Y | F | IC |
| Comparison Example 1 | | | | | | | | | +++ | ++ | 0 | 3 |
| Comparison Example 2 | | | | | | | | | +++ | ++ | 0 | 3 |
| Comparison Example 3 | | | | | | | | | 0 | 0 | +++ | 18 |
| 32 | +++ | +++ | 0 | 3 | +++ | 0 | ++ | 6 | + | 0 | 0 | 12 |
| 33 | +++ | +++ | 0 | 3 | +++ | 0 | ++ | 12 | 0 | 0 | 0 | 18 |

TABLE 2-continued

Microbiological results

| | Dilution % | | | | | | | | | | | |
|---|---|---|---|---|---|---|---|---|---|---|---|---|
| | 1.25 | | | | 2.5 | | | | 5 | | | |
| Example | B | Y | F | IC | B | Y | F | IC | B | Y | F | IC |
| 34 | +++ | ++ | 0 | 9 | ++ | ++ | 0 | 12 | + | 0 | 0 | 18 |
| 35 | ++ | ++ | 0 | 3 | ++ | ++ | 0 | 12 | 0 | 0 | 0 | 18 |
| 36 | +++ | 0 | 0 | 3 | +++ | 0 | +++ | 9 | 0 | 0 | 0 | 18 |
| 37 | ++ | ++ | 0 | 3 | + | 0 | 0 | 6 | ++ | + | 0 | 9 |
| 38 | +++ | ++ | 0 | 6 | 0 | 0 | 0 | 18 | 0 | 0 | 0 | 18 |
| 39 | +++ | +++ | 0 | 3 | +++ | ++ | + | 6 | +++ | + | 0 | 9 |
| 40 | +++ | ++ | 0 | 3 | ++ | ++ | 0 | 3 | + | + | 0 | 15 |
| 41 | +++ | ++ | 0 | 3 | ++ | + | 0 | 9 | ++ | + | 0 | 15 |
| 42 | +++ | ++ | 0 | 3 | +++ | + | 0 | 6 | ++ | 0 | 0 | 12 |
| 43 | +++ | 0 | 0 | 3 | ++ | 0 | 0 | 3 | ++ | 0 | 0 | 3 |
| 44 | +++ | +++ | 0 | 3 | +++ | 0 | 0 | 3 | ++ | 0 | 0 | 3 |
| 45 | +++ | +++ | 0 | 3 | +++ | +++ | 0 | 3 | +++ | ++ | 0 | 3 |
| 46 | +++ | +++ | 0 | 3 | ++ | ++ | 0 | 3 | ++ | ++ | 0 | 3 |
| 47 | +++ | +++ | 0 | 3 | +++ | +++ | 0 | 3 | +++ | ++ | 0 | 3 |
| 48 | +++ | ++ | 0 | 3 | ++ | ++ | 0 | 3 | ++ | ++ | 0 | 3 |
| 55 | ++ | ++ | + | 3 | 0 | 0 | 0 | 12 | 0 | 0 | 0 | 18 |
| 55a | ++ | ++ | 0 | 3 | 0 | 0 | 0 | 12 | 0 | 0 | 0 | 18 |
| 56 | ++ | ++ | +++ | 3 | + | + | + | 6 | + | + | + | 9 |
| 56a | ++ | ++ | 0 | 3 | + | + | 0 | 6 | + | + | 0 | 9 |
| 57 | ++ | ++ | ++ | 3 | 0 | 0 | + | 6 | 0 | 0 | + | 18 |
| 57a | ++ | ++ | 0 | 6 | + | + | 0 | 12 | 0 | 0 | 0 | 18 |
| 58 | 0 | 0 | + | 3 | 0 | 0 | + | 12 | 0 | 0 | + | 18 |
| 58a | + | + | 0 | 6 | + | + | 0 | 12 | 0 | 0 | 0 | 18 |
| 59 | +++ | 0 | 0 | 3 | +++ | 0 | +++ | 9 | 0 | 0 | 0 | 18 |
| 59a | +++ | 0 | 0 | 3 | +++ | 0 | 0 | 9 | 0 | 0 | 0 | 18 |
| 60 | +++ | 0 | 0 | 3 | ++ | 0 | 0 | 9 | 0 | 0 | 0 | 18 |
| 60a | +++ | 0 | 0 | 3 | ++ | 0 | 0 | 9 | 0 | 0 | 0 | 18 |

+++ = severe attack - germ count/ml > $10^4$
++ = moderate attack - germ count/ml $10^3$–$10^4$
+ = slight attack - germ count/ml < $10^3$
0 = no attack
B = bacteria
Y = yeasts
F = fungi
IC = first germ attack after x inoculation cycles

We claim:

1. A method comprising using 1,3,5-triazine-2,4,6-tris-alkylaminocarboxylic acid amino esters and amides of the general formula

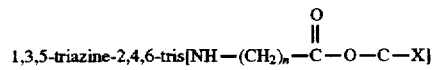

(I)

or

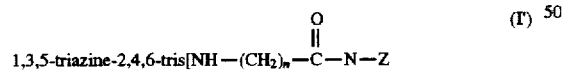

(I')

in which n denotes a number in the range from 4 to 11,

C—X is a radical of an alkanolamine of the general formula

(II)

wherein a carbon atom of the alkanolamine radical of formula 11 is directly bonded to an oxygen atom of the triazine as shown in formula (I), and N—Z is a radical of an alkanolamine of the general formula

(II')

wherein the nitrogen atom of the alkanolamine radical of formula II' is directly bonded to an oxygen atom of the triazine as shown in formula (I'), in which at least one of the groups $R^1$ is a) a hydroxyalkyl group having 2 to 4 carbon atoms, b) a hydroxyalkyl-oxyalkylene group having 2 to 4 carbon atoms in each of the hydroxyalkyl and oxyalkyl radicals or c) a dihydroxyalkyl group having 3 to 6 carbon atoms, and (i) in the case of the general formula (II), if less than three of the $R^1$ groups have the above meaning, the other $R^1$ groups are hydrogen, or if one of the $R^1$ groups has the above meaning, a second $R^1$ group is an alkyl group having 1 to 6 carbon atoms and a third $R^1$ group is hydrogen and, (ii) in the case of general formula (II'), if only one of the $R^1$ groups have the above meaning, the other $R^1$ group is hydrogen, as biocidal and biostatic agents in aqueous systems.

2. The method according to claim 1 wherein n is 5.

3. The method according to claim 1 wherein the amines of the general formula (II) and (II') are primary alkanolamines or mixtures of primary and secondary alkanolamines having 2 to 4 carbon atoms in the hydroxyalkyl group.

4. The method according to claim 1 further comprising the step of adding to said aqueous system a water-soluble fungicide which is stable to alkali.

5. The method according to claim 4 wherein said fungicide is pyrithione, a pyrithione derivative, N-alkyldiazenium dioxide salts or a mixture thereof.

6. The method according to claim 1 wherein said aqueous systems are cooling lubricants.

7. The method according to claim 1 wherein said aqueous system, based on the total formulation, contains 0.05 to 0.40% by weight of the 1,3,5-triazine-2,4,6-tris-alkylaminocarboxylic acid derivatives of the general formulas (I) or (I') and 0.0001 to 0.2% by weight of fungicides.

* * * * *